(12) United States Patent
Hanefeld et al.

(10) Patent No.: US 10,561,622 B2
(45) Date of Patent: Feb. 18, 2020

(54) PREPARATION OF NANOPARTICLES-RELEASING ENTERIC MICROPARTICLES

(71) Applicant: Merck Patent GmbH, Darmstadt (DE)

(72) Inventors: Andrea Hanefeld, Darmstadt (DE); Markus Weigandt, Mannheim (DE); Stefan Schiller, Darmstadt (DE); Marc Schneider, Saarbruecken (DE); Michael C. Lehr, Saarbruecken (DE)

(73) Assignee: Merck Patent GmbH, Darmstadt (DE)

( * ) Notice: Subject to any disclaimer, the term of this patent is extended or adjusted under 35 U.S.C. 154(b) by 365 days.

(21) Appl. No.: 15/522,530

(22) PCT Filed: Oct. 15, 2015

(86) PCT No.: PCT/EP2015/002033
§ 371 (c)(1),
(2) Date: Apr. 27, 2017

(87) PCT Pub. No.: WO2016/066249
PCT Pub. Date: May 6, 2016

(65) Prior Publication Data
US 2017/0312229 A1 Nov. 2, 2017

(30) Foreign Application Priority Data

Oct. 28, 2014 (EP) .................................. 14003650

(51) Int. Cl.
*A61K 9/50* (2006.01)
*A61K 9/51* (2006.01)

(52) U.S. Cl.
CPC .......... *A61K 9/5089* (2013.01); *A61K 9/5026* (2013.01); *A61K 9/5073* (2013.01); *A61K 9/5115* (2013.01); *A61K 9/5153* (2013.01)

(58) Field of Classification Search
CPC .................................................... A61K 9/5089
See application file for complete search history.

(56) References Cited

U.S. PATENT DOCUMENTS

2010/0310660 A1* 12/2010 Tsai ..................... A61K 9/0075
424/489
2013/0302429 A1 11/2013 Loo et al.

FOREIGN PATENT DOCUMENTS

WO 2012/071013 A1 5/2012

OTHER PUBLICATIONS

Thaduvai et al. "Process Validation of Pantoprazole 40mg tablets". The Pharma Innovation. vol. 1, No. 5 2012 pp. 47-62 (Year: 2012).*
Beck et al. Nanoparticle-coated microparticles :preparation and characterization. Journal of Microencapsulation Micro and Nano Carriers. 21:5 pp. 499-512. 2008 (Year: 2008).*

(Continued)

*Primary Examiner* — Cachet I Proctor
(74) *Attorney, Agent, or Firm* — Millen White Zelano & Branigan

(57) ABSTRACT

The present invention is directed to a process for the preparation of enteric microparticles comprising nanoparticles, wherein the nanoparticles comprise a matrix and an active ingredient. The microparticles obtained by such process are usable various multiparticulate pharmaceutical formulations such as extemporaneous dosage forms (powder for reconstitution).

25 Claims, 3 Drawing Sheets

(56) References Cited

OTHER PUBLICATIONS

Shastri et al. Implemeation of mixture design for formulation of albumin contaiing enteric-coated psray-dried microparticles. Drug Development and Industry Pharmacy. 39:2, pp. 164-175. May 2012 (Year: 2012).*

International Search Report dated Jan. 15, 2016, issued in corresponding PCT/EP2015/002033, 4 pages.

Al-Qadi, S. et al., "Microspheres loaded with polysaccharide nanoparticles for pulmonary delivery: Preparation, structure and surface analysis", Carbohydrate Polymers, vol. 86, No. 1, Mar. 11, 2011, pp. 25-34.

Kreuter, J. et al., "Long-Term Studies of Microencapsulated and Adsorbed Influenza Vaccine Nanoparticles", Journal of Pharmaceutical Sciences, vol. 70, No. 4, Apr. 1, 1981, pp. 367-371.

Al-Qadi, S. et al., "Microencapsulated chitosan nanoparticles for pulmonary protein delivery: In vivo evaluation of insulin-loaded formulations", Carbohydrate Polymers, vol. 86, No. 1, Mar. 11, 2011, pp. 25-34.

Grenha, A., et al., "Microencapsulated chitosan nanoparticles for lung protein delivery", European Journal of Pharmaceutical Sciences, vol. 25, No. 4-5, Jul. 1, 2005, pp. 427-437.

* cited by examiner

PREPARATION OF NANOPARTICLES-RELEASING ENTERIC MICROPARTICLES

The present invention is directed to a process for the preparation of enteric microparticles comprising nanoparticles, wherein the nanoparticles comprise a matrix and an active ingredient. The microparticles obtained by such process are usable for various multiparticulate pharmaceutical formulations such as extemporaneous dosage forms (powder for reconstitution).

Enteric microparticles retain their enteric properties upon reconstitution in acidic media (pH 3-5) thus protecting the encapsulated nanoparticles from the gastric environment (pH, mucus entrapment). After neutralization in the intestine, nanoparticles are released from the microparticles in the lumen to subsequently cross the intestinal epithelium. Depending on the nanoparticles' design, the active ingredient may be released and elicit a local effect, or enter the blood stream for systemic effect. Nanoparticles for vaccination purposes would be taken up by immunocompetent cells and release the active ingredient (e.g. peptides, proteins, or nucleic acids) to the cytosol, where the active ingredient is processed and the corresponding epitope is presented on the cells' surfaces to elicit an immune response.

Multiparticulate pharmaceutical formulations when applied as oral suspension have several advantages over oral monolithic dosage forms: They can be easily swallowed and are thus very suitable to be applied to infants or babies as well as to patients suffering from dysphagia (elderly, following chemotherapy etc.); they have a pylorus-independent gastric transit, which lowers the intra- and interindividual variability and avoids food effects; and they are suitable for easy and accurate animal dosing in pre-clinical studies or animal therapeutics.

Krishnamachari et al. describes the preparation of enteric coated budesonide-loaded PLGA microparticles using an o/o emulsion evaporation method (Krishnamachari, Y., et al. (2007): Development of pH- and time-dependent oral microparticles to optimize budesonide delivery to ileum and colon; International Journal of Pharmaceutics 338(1-2): 238-247). In such method the enteric polymer (Eudragit® S-100) is dissolved in a suitable solvent that does not dissolve the budesonide-loaded PLGA microparticles to be encapsulated and such solution is mixed with the budesonide-loaded PLGA microparticles and emulsified into a viscous oily liquid (liquid paraffin containing 1% (w/v) Span 85 as emulsifier). In subsequent solvent evaporation step the solvent evaporates or disperses into the oil and the enteric polymer precipitates around the nanoparticles. The enteric microparticles obtained are filtered, washed with a further solvent (n-hexane) and dried in vacuum.

The multistep approach described by Krishnamachari has several disadvantages. Firstly, the filtration step is rather time-consuming due to the non-volatile, very viscous dispersant (liquid paraffin) and the very small pore sizes of the filter needed for retention of the microparticles. Secondly, the washing step involves an excess of a further solvent (n-hexane), which has to be removed thereafter. Thirdly, the overall process is difficult to be up-scaled.

Nassar et al. describes the preparation of enteric coated docetaxel-loaded PLGA microparticles using spray-drying (Nassar, T., et al. (2011): High plasma levels and effective lymphatic uptake of docetaxel in an orally available nano-transporter formulation; Cancer Research 71(8): 3018-3028). In such method enteric polymer Eudragit® L 100-55 (soluble above pH 5.5) and hydroxypropyl methylcellulose (HPMC; solubility pH independent) are dissolved in phosphate buffer which is adjusted to pH 6.5. Such solution is mixed with an undisclosed amount of Poly(lactide-co-glycolide) nanocapsules (PLGA-NC) and spray dried at 160° C. inlet and 98° C. outlet temperature. The composition of the coating matrix applied to the PLGA-NCs as obtained by the process consists of 40% (w/w) Eudragit® L 100-55, 53% (w/w) HPMC and 7% sodium phosphates.

The enteric properties of the microparticles obtained by the process described by Nassar et al. remain to be questionable. Firstly, HPMC which contributes 53% (w/w) to the total mass of the coating is a nonionic polymer with a pH independent solubility. Secondly, the spray-drying process is performed with an outlet temperature of 98° C. As the spray dried product usually reaches a similar temperature this may cause damage to the particulate formulation, especially to the active ingredient but also to NCs as PLGA usually has a glass transition temperature well below 98° C. Thirdly, the pH of the spraying solution is adjusted to 6.5 with NaOH. As Eudragit® L 100-55 dissolves above pH 5.5, most of such polymer's methacrylic acid groups are deprotonized so that in the spray dried matrix Eudragit® is predominantly present as sodium salt. However, upon reconstitution of the dried microparticles in acidic media, the sodium methacrylate groups lead at first to a partial solvation of the polymer, followed by reprotonation and desolvation, thus leading to swelling and stickiness of the enteric microparticles in suspension. Such effect is even increased by the buffering salts that remain present from the spray-drying solution and which may affect the pH microclimate inside and in the vicinity of the enteric particles. Indeed, as evidenced by scanning electron micrographs the particles obtained by such process are hollow or collapsed (see FIG. 2A of Nassar et al.), which results in an unfavorable surface-to-volume ratio and protrusion of nanocapsules from the enteric matrix. As shown by FIG. 2B the particles are further interconnected after incubation at pH 1.2 for one hour (which pH is comparable to gastric passage), which most likely results from partial solvation and swelling due to excess neutralization as described above. Due to the particles' stickiness in acidic media it is most likely that they cannot be homogeneously dispersed to form a suspension for oral application (enteric microparticles for reconstitution and oral use should be redispersed in slightly acidic solvents having a pH below the solubility threshold of the enteric polymer (e.g. a pH of about 4) to avoid partial salvation/swelling of the microparticles upon their reconstitution). When delivered directly to the stomach in dry form (e.g. as powder in capsule), swelling and sticking of the particles would lead to a partial or complete loss of the described advantages of multiparticulate versus monolithic dosage forms.

As described the processes known in the art for the production of enteric microparticles comprising nanoparticles have several disadvantages and/or lead to particulate formulations with insufficient properties. It was the object of the present invention to provide a process for the production of enteric microparticles comprising nanoparticles that overcome such disadvantages. The process for production should be easily workable, fast, up-scalable and should lead to a microparticulate formulation that is easily dispersible in aqueous media. Further, the microparticles should maintain their integrity in acidic media (which they have to pass during passage of stomach) and should be able to release the nanoparticles dispersed therein at a pH greater than about 5.5 (as it is present in the intestinal environment) in a reproducible manner without substantial change to the mean particle size and size distribution.

Surprisingly, it has been found by the present invention that a process meeting such criteria can be made available when the nanoparticles to be contained in the enteric microparticles are suspended in a colloidal dispersion of the enteric coating material and spray-dried or when a suspension of the nanoparticles and a colloidal dispersion of the enteric coating material are co-spray-dried. Accordingly, one object of the present invention is directed to a process for the preparation of enteric microparticles comprising nanoparticles, wherein the nanoparticles comprise a matrix and an active ingredient, such process comprises (i) spray-drying of a suspension of the nanoparticles in a colloidal dispersion of the enteric coating material or (ii) co-spray-drying of a suspension of nanoparticles and a colloidal dispersion of the enteric coating material.

As used herein, "a" or "an" shall mean one or more. As used herein when used in conjunction with the word "comprising," the words "a" or "an" mean one or more than one. As used herein "another" means at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−1-3% of the recited value) that one of ordinary skill in the art would consider equivalent to the recited value (e.g., having the same function or result). In some instances, the term "about" may include numerical values that are rounded to the nearest significant figure.

The term "microparticles" as used herein refers to particles having a mean size of more than 1 μm. The microparticles can have a regular shape, such as spheres, or an irregular shape. The microparticles are built up of nanoparticles and an enteric polymer that embed the nanoparticles and provides a matrix for them to form microparticles having a sufficient physical stability required for their respective use.

The term "enteric coating" as used herein generally refers to a barrier applied to oral medication that controls the location in the digestive system where it is absorbed. Enteric refers to the small intestine, therefore enteric coatings prevent release of medication before it reaches the small intestine. The term "enteric" together with "microparticles" as used herein refers to that each of the microparticles is comprised of a matrix that prevents the release of the nanoparticles before the formulation reaches the small intestine. Enteric coatings work by presenting a surface that is stable at the highly acidic pH present in the stomach, but breaks down rapidly at a less acidic (relatively more basic) pH. For example, enteric coatings do not dissolve in the acidic juices of the stomach (pH 1-3) but in the higher pH (above pH 5.5) environment present in the small intestine. The term "enteric coating material" as used herein refers to a material having the properties as described for enteric coating. Such material can be used to embed the nanoparticles and to form the microparticles of the invention and to protect them from degradation during passage of the stomach after oral application.

The term "nanoparticles" as used herein refers to particles having a mean size of less than 1 μm. The nanoparticles preferably have a regular shape, such as spheres, but may also have an irregular shape.

The term "matrix" as used herein generally refers to a surrounding substance within which something else is contained. For purposes herein, a matrix refers to the structural properties or architecture of a solid in which other components can be dispersed. In the microparticles of the invention the matrix is provided by the enteric coating material in which the nanoparticles are dispersed.

The term "active ingredient" means any ingredient that provides a pharmacological or biological effect when applied to a biological system. The active ingredient may be a pharmaceutical drug, biological matter of viral or ling origin. Examples of an active ingredient that may be used in the process of the present inventions are insulin, heparin, calcitonin, hydrocortisone, prednisone, budesonide, methotrexate, mesalazine, sulfasalazine, amphotericin B, nucleic acids, or antigens (peptides, proteins, sugars, or other substances that form surfaces recognized by the immune system, either produced, extracted, or homogenized from tissue, an organism or a virus).

The term "colloidal" as used herein refers to a state of subdivision, implying that the molecules or polymolecular particles dispersed in a medium have at least, in one direction, a dimension roughly between 1 nm and 1 μm, or that in a given system, discontinuities are found at distances of that order (1972, 31, 605, IUPAC Compendium of Chemical Terminology, 2nd Edition, 1997). The term "colloidal dispersion" as used herein refers to a system in which solid particles of colloidal size are dispersed in a continuous liquid phase, preferably in an aqueous phase.

The term "suspension" as used herein refers to a liquid containing one or more components dispersed therein, wherein the components are substantially not dissolved in the liquid. In this context the term substantially means a proportion of at least about 90%, at least 95%, at least about 98%, at least 99% or more. In some embodiments the term substantially includes 100%. In the process of the invention a suspension of nanoparticles in an aqueous solvent is prepared.

The term "spray-drying", as used herein, refers to a method of producing a dry powder comprising micron-sized particles from a solution or suspension by using a spray-dryer. Spray-drying is, in principle, a solvent extraction process. The constituents of the product to be obtained are dissolved/dispersed in a liquid and then fed, for example by using a peristaltic pump, to an atomiser of a spray-dryer. A suitable atomizer which can be used for atomization of the liquid, include nozzles or rotary discs. With nozzles, atomization occurs due to the action of the compressed gas, while in case of using rotary discs atomization occurs due to the rapid rotation of the disc. In both cases, atomization leads to disruption of the liquid into small droplets into the drying chamber, wherein the solvent is extracted from the aerosol droplets and is discharged out, for example through an exhaust tube to a solvent trap.

Drop sizes from 1 to 500 μm can be generated by spray-drying. As the solvent (water or organic solvent) dries, the nanoparticles-containing droplets dries into a micron-sized particle, forming powder-like particles.

A number of commercially available spray drying machines can be used to prepare the microparticles of the invention, for example, suitable machines are manufactured by Buchi and Niro. Examples of suitable spray-driers include lab scale spray-dryers from Buchi, such as the Mini Spray Dryer 290, or a MOBILE MINOR™, or a Pharma Spray Dryer PharmaSD® from Niro, or a 4M8-TriX from Procept NV.

In a typical spray drying machine the suspension to be dried is pumped from a stirred reservoir to an atomization chamber where it is sprayed from a nozzle as fine droplets (preferably the droplets are in the range of 1 to 20 µm in diameter) into a stream of heated air, for example, inlet temperatures in the range of 50 to 150° C. (nitrogen can be used in place of air if there is a risk of undesirable oxidation of the product). The temperature of the heated air must be sufficient to evaporate the liquid and dry the microparticles to a free flowing powder but should not be so high as to degrade the product. The microparticles may be collected in a cyclone or a filter or a combination of cyclones and filters.

The term "co-spray-drying", as used herein, refers to a method of producing a dry powder comprising micron-sized particles from two or more solutions or suspensions by using a spray-dryer. This method differs from conventional spray drying as described above in that the solutions or suspensions are fed separately to the atomizing device without prior bulk mixing. The separate feeds are brought into contact just in or after the atomizing device. An example of a suitable spray dryer would be a Micro Mist Spray Dryer from Fujisaki Electric.

Suitable spray-drying techniques, which can be used for preparation of the microparticles, are well known and described, for example, by K. Masters in "Spray-drying Handbook", John Wiley & Sons, New York, 1984. In a preferred embodiment, atomization of the liquid is performed by using a nozzle.

In the process of the invention spray-drying of the suspension of nanoparticles in a colloidal dispersion of enteric coating material leads to microparticles wherein the nanoparticles are embedded in a matrix of the enteric coating material.

According to a preferred embodiment of the invention the process comprises the following steps: (a) preparing an aqueous dispersion comprising an enteric coating material; (b) adjusting the pH of the aqueous dispersion prepared by step (a) to a pH slightly below the solubility threshold of the enteric coating material to produce a colloidal dispersion of the enteric coating material; (c) mixing the nanoparticles with the colloidal dispersion prepared by step (b) to produce a suspension of the nanoparticles in such colloidal dispersion; and (d) spray-drying the colloidal dispersion prepared by step (c). Accordingly the invention is also directed to a process comprising the steps (a) preparing an aqueous dispersion comprising an enteric coating material;

(b) adjusting the pH of the aqueous dispersion prepared by step (a) to a pH slightly below the solubility threshold of the enteric coating material to produce a colloidal dispersion of the enteric coating material;

(c) mixing the nanoparticles with the colloidal dispersion prepared by step (b) to produce a suspension of the nanoparticles in such colloidal dispersion;

(d) spray-drying the colloidal dispersion prepared by step (c).

For preparation of the aqueous dispersion in accordance to step (a) the enteric coating material is dispersed in an aqueous solvent. The dispersion can be facilitated using suitable techniques known in the art such as stirring or sonification. The term "aqueous solvent" as used herein also refers to water, or a mixture of solvents that contains at least about 50% or 50%, at least about 60% or 60%, at least about 70% or 70%, or about or at 75%, 80%, 85%, 90%, 95%, 96%, 97%, 98%, 99% or higher amounts of water. The aqueous solvent may contain salts, buffers or other solutes that are soluble in water. Preferably the aqueous solvent is water.

In step (b) the pH is adjusted to a pH slightly below the solubility threshold of the enteric coating material by adding a pH increasing agent. The solubility threshold as used herein refers to the pH, at which the material begins to dissolve. The solubility threshold is a characteristic of a enteric coating material and is usually given by the manufacturer for a specific material, for example, the enteric coating material Eudragit® L 100-55 is defined to have a solubility threshold of pH 5.5. When increasing the pH in step (b) the enteric coating material dispersed in the aqueous solvent to a pH slightly below the solubility threshold the enteric coating material gets partially deprotonated. The rising surface charge of the dispersed particles and the resulting interparticulate repulsive forces lead to the formation and stabilization of a colloidal dispersion of the enteric coating material. The colloidal dispersion that is prepared by step (b) is characterized by the disappearance of visible particulates and the formation of a homogeneous, milky-white fluid. Preferably, the particle size of the dispersed enteric coating material is below 1 µm. Suitable methods for the determination of the particle size include static light scattering, dynamic light scattering and electron microscopy.

In one embodiment of the invention the colloidal dispersion obtained in step (b) has a degree of neutralization (DN) of 5 to 40%, preferably 1 to 30%, more preferably 12 to 25% and most preferably about 15%. Therefore, the invention is also directed to a process, which is characterized in that the colloidal dispersion obtained in step (b) has a degree of neutralization (DN) of 5 to 40%, preferably 1 to 30%, more preferably 12 to 25% and most preferably about 15% The term "pH increasing agent" as used herein refers to an agent that increases the pH of the aqueous dispersion of enteric coating material when added to such aqueous dispersion. Suitable pH increasing agents are, for example, alkali metal hydroxides such as sodium hydroxide, potassium hydroxide, calcium hydroxide or magnesium hydroxide, carbonates and hydrogencarbonates of alkali metals such as sodium carbonate, potassium carbonate, sodium bicarbonate or potassium bicarbonate, ammonium carbonate, ammonium hydrogencarbonate, diethanolamine, monoethanolamine, triethanolamine, organic amine base, alkaline amino acids such as lysine or arginine, trolamine or $NH_3$. Preferably the pH increasing agent used for adjustment of pH in step (b) of the process described above are sodium hydroxide, potassium hydroxide, carbonates and hydrogencarbonates of alkali metals, ammonium carbonate, ammonium hydrogencarbonate, or ammonia, more preferably ammonia. Ammonia is especially preferred as evaporates under usual spray-drying conditions leading to that no cation stemming from the pH increasing agent remains in the microparticles after spray-drying.

It has been found that increasing amounts of alkali cations resulting from the pH increasing agent have a detrimental effect on re-dispersibilty of the spray-dried particles and lead to penetration of solvent and swallowing upon reconstitution in aqueous solutions. Therefore, it is preferred that the pH increasing agent is added in the least possible amount that allows a film formation that is sufficient to build up a flexible matrix for the nanoparticles dispersed therein, to protect them from agglomeration during spray-drying and to form microparticles in which the nanoparticles dispersed therein are protected from gastric environment upon oral administration to a mammal. Depending on the enteric coating material an appropriate pH value slightly below the solubility threshold that allows formation of the colloidal dispersion can be a pH value in the range from ≤1 to ≤0.01 less than the solubility threshold of the enteric coating material, a pH value in the range from ≤0.5 to ≤0.01 less than the solubility threshold of the enteric coating material, a pH value in range from ≤0.2 to ≤0.02 less than the solubility threshold of the enteric coating material or a pH value in the range from ≤0.1 to ≤0.05 less than the solubility threshold of the enteric coating material.

According to an alternative preferred embodiment of the invention the process comprises the following steps: (a) preparing an aqueous dispersion comprising an enteric coating material; (b) adjusting the pH of the aqueous dispersion prepared by step (a) to a pH slightly below the solubility threshold of the enteric coating material to produce a colloidal dispersion of the enteric coating material; (c) preparing an aqueous suspension comprising the nanoparticles; and (d) co-spray-drying of the colloidal dispersion prepared by step (b) together with the aqueous suspension prepared by step (c). Accordingly the invention is also directed to a process comprising the steps (a) preparing an aqueous dispersion comprising an enteric coating material;

(b) adjusting the pH of the aqueous dispersion prepared by step (a) to a pH slightly below the solubility threshold of the enteric coating material to produce a colloidal dispersion of the enteric coating material;

(c) preparing an aqueous suspension comprising the nanoparticles; and (d) co-spray-drying of the colloidal dispersion prepared by step (b) together with the aqueous suspension prepared by step (c).

According to a preferred embodiment of the invention the nanoparticles used in the process have a mean size from 20 nm to 1000 nm, preferably from 100 nm to 500 nm, and more preferably from 200 nm to 300 nm. Therefore, the invention is also directed to a process, which is characterized in that the nanoparticles used in the process have a mean size from 20 nm to 1000 nm, preferably from 100 nm to 500 nm, and more preferably from 200 nm to 300 nm.

The term "mean size" as used herein refers to the hydrodynamic average diameter ("z-average") of the nanoparticle population that moves together in an aqueous medium. The z-average is defined by ISO 22412 as the 'harmonic intensity averaged particle diameter'. To compare z-average sizes measured by different techniques the samples have to be monomodal (i.e. only one peak), spherical or near-spherical in shape and monodisperse (i.e. very narrow width of distribution). The mean size of these systems can be measured by standard processes known by the person skilled in the art, and which are described, for example, in the experimental part (see below).

The matrix material present in the nanoparticles used in the process of the invention can be any matrix material being suitable for dispersing, dissolving or embedding the active ingredient. In some embodiments of the invention, the nanoparticles comprise a biocompatible inorganic particulate material such as silica, surface-modified silica or a biocompatible organic polymer, preferably a biodegradable polymer. Therefore, the invention is also directed to the process of the invention, which is characterized in that the matrix of the nanoparticles is an inorganic particulate material such as silica, surface-modified silica or a biocompatible polymer, preferably a biodegradable polymer.

The term "biocompatible" as used herein refers to exhibition of essentially no cytotoxicity or immunogenicity while in contact with body fluids or tissues. The term "biocompatible" together with "inorganic particulate material" or "organic polymer" refers to material which are non-toxic, chemically inert, and substantially non-immunogenic when used internally in a subject and which are substantially insoluble in blood. As used herein, the term "organic polymer" refers to oligomers, co-oligomers, polymers and co-polymers, e.g., statistical, block, multiblock, star, grafted, gradient copolymers and combination thereof. The average molecular weight of the polymer, as determined by gel permeation chromatography, can range from 20,000 to about 500,000. The biocompatible organic polymer can be either non-biodegradable or preferably biodegradable.

The term "biodegradable" as used herein generally refers to be capable to be decomposed by the action of biological agents. A biodegradable polymer, as used herein, refers to a polymer that degrades or erodes in vivo to form smaller chemical species. Degradation can result, for example, by enzymatic, chemical and/or physical processes. Suitable biodegradable polymers include, for example, poly(lactic acid)s (PLA), poly(glycolic acid)s (PGA), copolymers of lactic acid and glycolic acid (PLGA), polycaprolactones (PLC), polyepsilon caprolactones, copolymers of lactic acid and caprolactone, polyhydroxy butyric acids, chitosans, polyesters, polycarbonates, polyesteramides, polyanhydrides, poly(amino acids), poly(ortho)ester, polyurethanes, polyanhydrides, polyacetyls, polydihydropyrans, polyamides, such as, for example, polyesteramides or polyaminoacids, polysaccharides polycyanoacrylates, polyetheresters, poly(dioxanone)s, poly(alkylene alkylate)s and copolymers of polyethylene glycol, blends and copolymers thereof and derivatives thereof such as pegylated polymers like PEG-PLGA.

In a preferred embodiment of the invention the matrix of the nanoparticles used in the process is a biodegradable polymer which is poly(lactic acid) (PLA), poly(glycolic acid) (PGA), polycaprolactone (PCL), a copolymer of lactic acid and glycolic acid (PLGA), a copolymer of lactic acid and caprolactone, polyepsilon caprolactone, polyhydroxy butyric acid, chitosan, a polyester, a poly(ortho)ester, a polyurethane, a polyanhydride, a polyacetal, a polydihydropyran, a polyamide, a polysaccharide or a polycyanoacrylate, a blend or copolymer thereof or a derivative thereof such as pegylated polymers like PEG-PLGA. Therefore, the invention is also directed to a process, which is characterized in that the biodegradable polymer is poly(lactic acid) (PLA), poly(glycolic acid) (PGA), polycaprolactone (PCL), a copolymer of lactic acid and glycolic acid (PLGA), a copolymer of lactic acid and caprolactone, polyepsilon caprolactone, polyhydroxy butyric acid, chitosan, a polyester, a poly(ortho)ester, a polyurethane, a polyanhydride, a polyacetal, a polydihydropyran, a polyamide, a polysaccharide or a polycyanoacrylate, a blend or copolymer thereof or a derivative thereof such as pegylated polymers like PEG-PLGA.

Especially preferred is PLGA as biodegradable polymer. Accordingly, the invention is further directed to a process, which is characterized in that the biodegradable polymer is PLGA.

The enteric coating material present used to produce the microparticles in the process of the invention can be any enteric coating material that is suitable for dispersing or embedding the nanoparticles used in the process. Preferred enteric coating material used in the process of the invention is cellulose acetate phthalate, hydroxypropyl methylcellulose phthalate, hydroxypropyl methylcellulose acetate succinate, polyvinyl acetate phthalate, carboxymethyl ethylcellulose, cellulose acetate trimellitate, a copolymer of acrylic or methacrylic acid and an acrylic or methacrylic ester, preferably a copolymer of methacrylic acid and a methacrylate or a acrylate ester. Therefore, the invention is further directed to a process, which is characterized in that the enteric coating material is cellulose acetate phthalate, hydroxypropyl methylcellulose phthalate, hydroxypropyl methylcellulose acetate succinate, polyvinyl acetate phthalate, carboxymethyl ethylcellulose, cellulose acetate trimellitate, a copolymer of acrylic or methacrylic acid and an acrylic or methacrylic ester, preferably a copolymers of methacrylic acid and a methacrylate or a acrylate ester. Copolymers of methacrylic acid and a methacrylate or a acrylate ester are commercially available under the trade name Eudragit® (Evonik Industries AG, Essen, Germany).

Especially preferred copolymers of methacrylic acid and methacrylate or acrylate esters that are usable in the process of the invention are (Poly(methacrylic acid-co-methyl methacrylate) (1:1) (e.g. Eudragit® L 100), (Poly(methacrylic acid-co-methyl methacrylate) (1:2) (e.g. Eudragit® S 100), Poly(methacrylic acid-co-ethyl acrylate) (1:1) (e.g. Eudragit® L 100-55). Accordingly, the invention is further directed to a process, which is characterized in that the copolymer of methacrylic acid and a methacrylate or acrylate ester is (Poly(methacrylic acid-co-methyl methacrylate) (1:1), (Poly(methacrylic acid-co-methyl methacrylate) (1:2), Poly(methacrylic acid-co-ethyl acrylate) (1:1).

The microparticles produced by the process of the invention have a mean size of 1 µm to 200 µm, preferably of 10 µm to 150 µm and more preferably of 50 µm to 150 µm. Thus the invention is also directed to a process, which is characterized in that the microparticles have a mean size of 1 µm to 200 µm, preferably of 10 µm to 150 µm and more preferably of 50 µm to 150 µm.

Advantageously, the parameters in the spray-drying step of the process of the invention are selected and controlled in a way as it is known in the art that the temperature of the dried product is never above the glass transition temperature of the nanoparticles, preferably at least 1° C. below, and more preferably at least 5° C. below the glass transition temperature of the nanoparticles. The product temperature may be calculated by computational fluid dynamics modeling based on device geometry and kinetic studies of the evaporation process in drying droplets (e.g. based on single droplet drying experiments), traced by infrared cameras, or estimated from the temperature at the outlet of the drying chamber. Thus the invention is also directed to a process, which is characterized in that the temperature of the dried product is never above the glass transition temperature of the nanoparticles, preferably at least 1° C. below, and more preferably at least 5° C. below the glass transition temperature of the nanoparticles.

Parameters that can be selected and varied during the spray-drying process to achieve the desired product temperature and as well as the effect of such parameters on the product temperature are well-known in the art and include, i.a. the kind and/or composition of solvent, the concentrations of starting materials, the flow-rates of the injected materials as well as of the drying gas, the inlet air temperature and inlet air humidity.

The term "glass transition temperature" generally refers to the temperature at which amorphous polymers undergo a transition from a rubbery, viscous amorphous liquid, to a brittle, glassy amorphous solid. A glass transition temperature as used herein refers to an intermediate point glass transition temperature obtained when the temperature is raised at a heating rate of 10 or 20° C. per minute using a differential scanning calorimeter (DSC).

The examples explain the invention without being restricted thereto.

Particle Size Analysis of Nanoparticles

Particle size measurements are performed using a Zetasizer Nano ZS (Malvern Instruments) applying dynamic light scattering (DLS). Using cumulants analysis, the z-average (harmonic intensity averaged particle diameter; z-av) and the polydispersity index (estimator of the particle size distribution width; PDI) were calculated according to ISO13321 and ISO22412, using a viscosity of 0.8872 mPas (at 25° C.) and a refractive index of 1.330. Each sample is equilibrated to 25° C. within 120 seconds and analysis is performed in triplicate.

Nanoparticles used for Preparation of Microparticles

Fluorescent ovalbumin loaded PLGA (Resomer® RG 503 H, Evonik) nanoparticles were used as model nanoparticles (PLGA-NP). They were prepared by a modified double emulsion solvent evaporation method (Blanco, M. D., et al. (1997): Development and characterization of protein-loaded poly(lactide-co-glycolide) nanospheres; Eur J Pharm Biopharm 43(3): 287-294) using polyvinyl alcohol as stabilizer and Coumarin 6 as fluorescent dye. In one embodiment modified PEG-PLGA was used to prepare nanoparticles (mod. PEG-PLGA-NP) according to the method described above. Mean particle sizes of different batches were between 150-300 nm.

Chitsosan nanoparticles are prepared by the ionic gelation method (Grenha, A. (2012): Chitosan nanoparticles: a survey of preparation methods; Journal of drug targeting 20(4): 291-300). Chitosan (Chitoscience, Heppe Medical Chitosan) is dissolved in an acidic acid solution and complexed by e.g. carboxymethylcellulose solution which is prepared by dissolving e.g. Tylose C30 (Hoechst) in purified water and added slowly to the chitosan phase while stirring on a magnetic stirrer.

Silica nanoparticles are prepared as described in EP 0216278 B1 by hydrolysis of tetraalkoxysilanes in aqueous-alcoholic-ammoniacal medium, where firstly a sol of primary particles is produced, and the SiO2 particles obtained are subsequently brought to the desired particle size by continuous metering-in of tetraalkoxysilane in a controlled manner corresponding to the extent of reaction. The production of 50 g of SiO2 particles having a size of 25 nm requires, for example, 1.2 l of EtOH as solubiliser, 860 ml of deionised water, 167 ml of tetraethyl orthosilicate and 28.5 ml of 25% aqueous ammonia solution.

Enteric Coating Material

Enteric polymers such as Methacrylic Acid Copolymers (e.g. Eudragit®) can be sprayed as organic solution (e.g. alcohols, acetone) to achieve a steady film upon drying. While the polymer molecules in solution can freely and ideally rearrange for film formation, the use of solvents in spray drying is less attractive due to environmental restrictions and related cost of equipment. Furthermore, preliminary studies showed that this method is not suitable for the intended purpose. Although alcohols are non-solvents for relevant polymeric nanoparticles (e.g. PLGA), mixing PLGA nanoparticles with a solution of Eudragit® L in ethanol leads to precipitation.

Although good films can also be produced from aqueous solutions of Eudragit®, the high viscosity is detrimental for nozzle spraying. Moreover, the films are made of polymer with largely neutralized methacrylic acid groups. Contrary to the free acid, Eudragit® salts are freely soluble in purified, buffer-free water. When dispersing particles made from Eudragit® salts in acidic media they will immediately begin to swell, forming sticky gel-like lumps before the protonation of the methacrylate groups by the medium stops the dissolution process.

Processing without organic solvents is possible by using aqueous dispersions of Eudragit® which are stabilized electrostatically by partial deprotonation of the methacrylate groups. Upon drying of the coating the Eudragit® particles are eventually held together by capillary forces, but particle coalescence is needed to form a closed film. Therefore, a plasticizer is always added to spray suspensions. However, a plasticizer might also facilitate the coalescence of encapsulated nanoparticles during processing and product storage by decreasing the glass transition temperature of the PLGA-NP (Kranz, H., et al. (2000): Physicomechanical properties of biodegradable poly(D,L-lactide) and poly(D,L-lactide-co-glycolide) films in the dry and wet states; Journal of Pharmaceutical Sciences 89(12): 2899-2605). Hence a plasticizer-free formulation is preferred.

It has been found that the addition of plasticizer can be avoided when the enteric polymer dispersed in an aqueous solvent is partially neutralized to an extent that leads to that the aqueous dispersion of the enteric polymer is converted to a colloidal dispersion of it as demonstrated in the following.

Using Eudragit® L as an enteric polymer aqueous spray dispersions having different degrees of neutralization (DN) were tested. The term "degree of neutralization" or "DN" of a polymer as used herein refers to the mole ratio of added $NH_3$ to the total polymer carboxylic acid groups present in the solution.

Partially neutralized Eudragit® dispersions with a DN of 6% or 15% and a clear, viscous Eudragit® solution with a DN of 70% were prepared by suspending Eudragit® in purified water and adding the appropriate amount of 1 M ammonia solution dropwise under stirring to yield a concentration of 100 mg/mL Eudragit®.

To prepare a dispersion of Eudragit® L with a degree of neutralization of 6%, 2.5 g Eudragit® L 100 are dispersed in 20 mL purified water by magnetic stirring. After 5 min stirring, 0.85 mL of 1 N ammonia solution is added dropwise with a syringe pump over 10 min. The dispersion is diluted with purified water to 25.0 g and stirred for 60 min to yield a homogeneous milky white dispersion of 10% (w/w) Eudragit® L without visible particles or lumps. The pH of the dispersion is 5.56, thus below the solubility threshold of Eudragit® L (pH 6.0).

To prepare a dispersion of Eudragit® L with a degree of neutralization of 15%, 2.5 g Eudragit® L 100 are dispersed in 20 mL purified water by magnetic stirring. After 5 min stirring, 2.11 mL of 1 N ammonia solution is added dropwise with a syringe pump over 10 min. The dispersion is diluted with purified water to 25.0 g and stirred for 60 min to yield a homogeneous milky white dispersion of 10% (w/w) Eudragit® L without visible particles or lumps. The pH of the dispersion is 5.88 thus below the solubility threshold of Eudragit® L (pH 6.0).

To prepare a solution of Eudragit® L with a degree of neutralization of 70%, 2.5 g Eudragit® L 100 are dispersed in 10 mL purified water by magnetic stirring. After 5 min stirring, 9.85 mL of 1 N ammonia solution is added dropwise with a syringe pump over 10 min. The dispersion is diluted with purified water to 25.0 g and stirred for 60 min to yield a clear, viscous solution of 10% (w/w) Eudragit® L. The pH of the dispersion is 6.09, thus above the solubility threshold of Eudragit® L (pH 6.0). Dispersions of further enteric coating materials are prepared in a similar manner by calculating the amount of base needed for a specific DN from the acid value of the enteric coating material (usually provided as mg KOH per g polymer or similar).

Preparation of Microparticles (General Description)

Spray feeds were prepared by mixing PLGA nanoparticle suspensions with partially neutralized Eudragit® dispersions to yield a total solid content of 55-80 mg/g spray feed. For screening purposes, volume equivalents to 200 mg dry substance were dried with a lab scale spray dryer (4M8-TriX, ProCepT, Zelzate, Belgium) using a feed rate of 6 mL/min, a 0.4 mm bi-fluid nozzle with 20 L/min atomizing air flow, 80±2° C. inlet temperature, 400 L/min drying air flow, 150 L/min cooling air flow, and 32-38° C. outlet temperature. As PLGA has a relatively low glass transition temperature (44-48° C. for RG 503 H), a low outlet temperature is preferred to avoid nanoparticle deformation or agglomeration. Experiments were performed at 20-22° C. ambient temperature and 51-60% relative humidity. The microparticles have a final composition as shown in table 1.

TABLE 1

Composition of enteric microparticles prepared by spray drying

| Component | Mass percent (dry mass) of final formulation |
|---|---|
| Eudragit ® L 100 | 90% |
| PLGA-NP | 10% |

Further Microparticles are prepared analogously having the composition as given in table 2:

TABLE 2

Composition of enteric microparticles prepared by spray drying

| Example | Component | Mass percent (dry mass) of final formulation |
|---|---|---|
| 1 | Eudragit ® L 100 | 80% |
|   | PLGA-NP | 20% |
| 2 | Eudragit ® S 100 | 90% |
|   | PLGA-NP | 10% |
| 3 | Eudragit ® L 100 D-55 | 80% |
|   | PLGA-NP | 20% |
| 4 | Eudragit ® L 100 | 90% |
|   | Mod.PEG—PLGA-NP | 10% |
| 5 | Eudragit ® L 100 D-55 | 90% |
|   | Chitosan-NP | 10% |
| 6 | Eudragit ® L 100 D-55 | 90% |
|   | Silica-NP | 10% |

Alternatively, microparticles can be prepared by co-spray-drying. For this process, a PLGA nanoparticle suspension and a partially neutralized Eudragit® dispersion are fed separately to the atomizing device and spray dried under suitable conditions as described above.

The formulations were evaluated for the feasibility to produce homogeneous suspensions in acidic media by hand shaking, vortexing and bath sonication. The size of nanoparticles before processing and after release in phosphate buffered saline pH 6.8 was determined by dynamic light scattering to identify possible agglomeration (Table 3).

TABLE 3

Properties of nanoparticle-releasing enteric microparticle formulations prepared from Eudragit ® L 100 with different degrees of neutralization. Meaning of symbols for the dispersibility of the enteric microparticles in HCl: "++": readily dispersible by shaking or vortex; "+": dispersible by bath sonication; "−": not dispersible

| Degree of Neutralization | PLGA-NP mass percent | Dispersibility in 0.1M HCl | Z-av | PDI |
|---|---|---|---|---|
| Before spray drying | | | 217 nm | 0.26 |
| 6% | 10% | ++ | 379 nm | 0.39 |
| 6% | 20% | ++ | 655 nm | 0.55 |
| 15% | 10% | + | 257 nm | 0.26 |
| 15% | 20% | + | 290 nm | 0.34 |
| 15% | 33% | + | 1847 nm | 0.60 |
| 70% | 10% | − | 259 nm | 0.24 |
| 70% | 20% | − | 229 nm | 0.23 |
| 70% | 33% | − | 484 nm | 0.57 |

As shown in Table 3, formulations with DN 6% released only agglomerated nanoparticles, while enteric microparticles prepared with DN 70% underwent gelling and lumping in acidic media. Formulations with DN 15% and a nanoparticle content of 10% (m/m) release NP at pH 6.8 with a size distribution similar to the untreated NP (Table 3). This indicates that the proposed method does not alter the favorable target product profile of the encapsulated NP. Furthermore, these formulations are homogeneously dispersible in 0.1 M HCl and as such suitable as extemporaneous dosage form for reconstitution in acidic media prior to administration.

Scanning electron micrographs show that DN 6% does not lead to a closed film as revealed by the black spaces between individual Eudragit® particles (FIG. 1A). Surprisingly, by raising the DN to 15% the particles are now completely bridged, suggesting a closed film and a superior matrix for the protection and spacing of encapsulated PLGA nanoparticles (FIG. 1B). Enteric particles prepared from aqueous Eudragit® solutions (DN 70%) exhibit a smooth surface from film formation (FIG. 1C; the wrinkles are measurement artifacts caused by the shrinkage of the particles under the electron beam).

In one example, enteric microparticles were prepared from modified PEG-PLGA-NP and Eudragit® L 100 using DN 30%. The formulation was characterized as described above. The microparticles could be reconstituted homogeneously in 0.1 M HCl, while the PEG-PLGA-NP were released at pH 6.8 with an acceptable increase of the mean particle size and only a minor broadening of the particle size distribution (Table 4).

TABLE 4

Properties of nanoparticle-releasing enteric microparticle formulations prepared from Eudragit ® L 100 and modified PEG-PLGA-NP.

| Degree of Neutralization | Dispersibility in 0.1M HCl | Z-av | PDI |
|---|---|---|---|
| Before spray drying | | 230 nm | 0.13 |
| 30% | + | 325 nm | 0.19 |

Figure 1A:
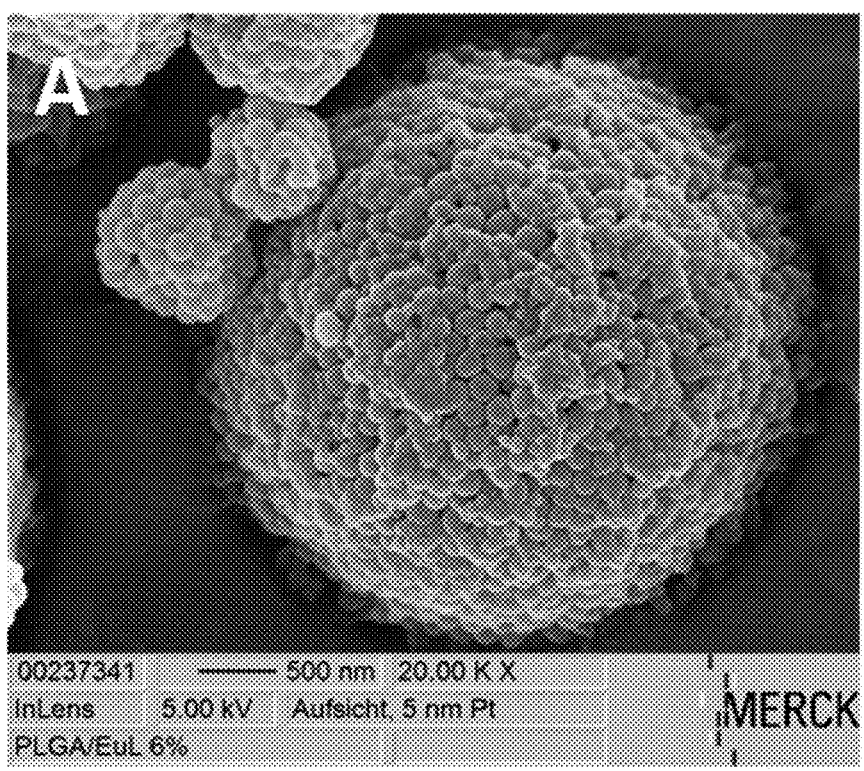
FIGS. 1A, 1B and 1C are scanning electron micrographs
Figure 1B:
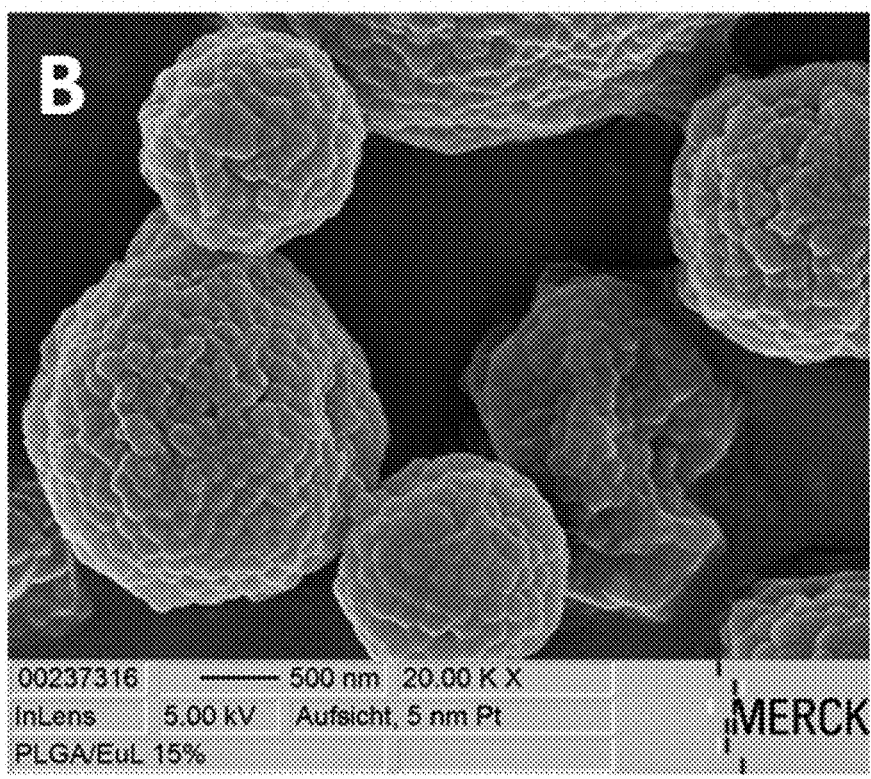
Figure 1C:
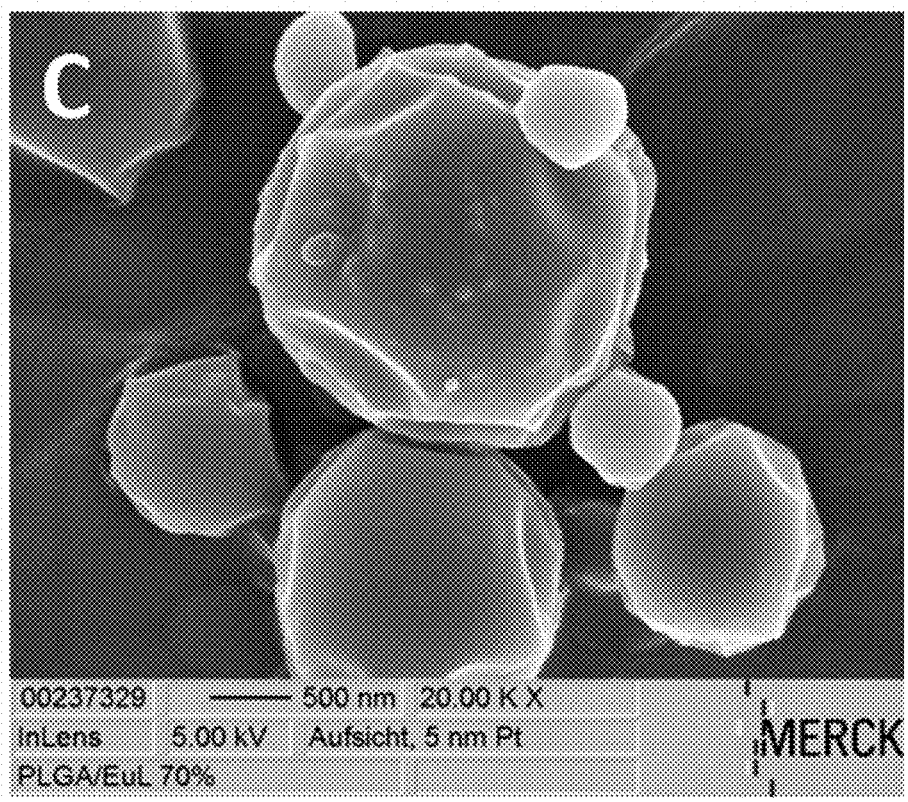
Figure 2:
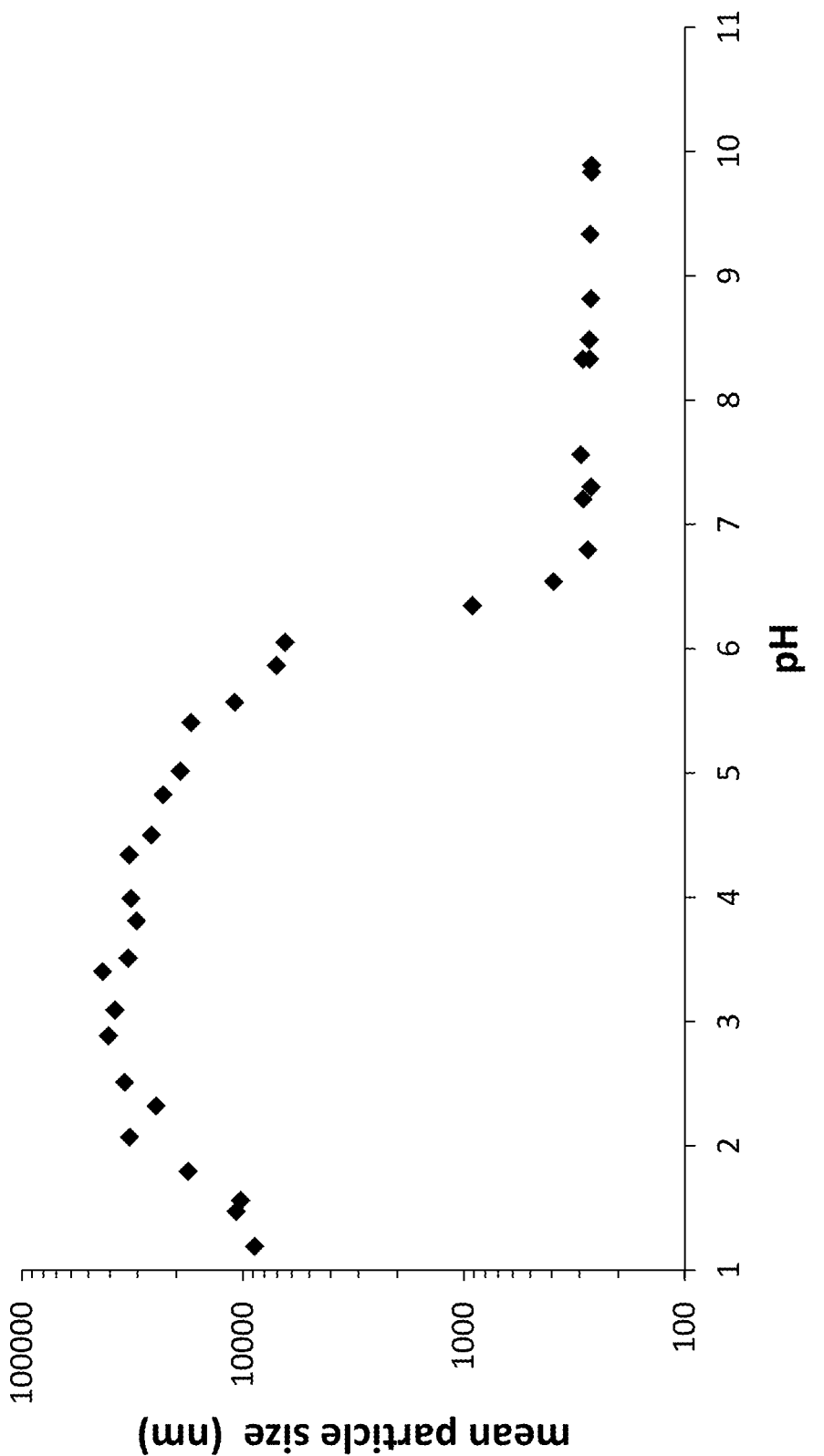
FIG. 2 is a graph
In-vitro Release of NP from the Enteric Microparticles To study the enteric properties of the formulation, 20 mg enteric microparticles were homogeneously dispersed in 10 mL 0.1 N HCl. The mean particle size was measured by dynamic light scattering while incrementally raising the pH by addition of NaOH. As expected, particle size drastically decreases above pH 6, indicating the dissolution of the enteric microparticles and the release of the PLGA nanoparticles (see FIG. 2 showing pH titration vs. particle size of nanoparticle-releasing enteric microparticles prepared with DN 15%).

The invention claimed is:

1. A process for the preparation of enteric microparticles comprising nanoparticles, wherein the nanoparticles comprise a matrix and an active ingredient, such process comprises (i) spray-drying of a suspension of the nanoparticles in a colloidal dispersion of an enteric coating material or (ii) co-spray-drying of a suspension of nanoparticles and a colloidal dispersion of the enteric coating material.

2. The process according to claim 1, comprising
 (a) preparing an aqueous dispersion comprising an enteric coating material;
 (b) adjusting the pH of the aqueous dispersion prepared by step (a) to a pH slightly below the solubility threshold of the enteric coating material to produce a colloidal dispersion of the enteric coating material;
 (c) mixing the nanoparticles with the colloidal dispersion prepared by step (b) to produce a suspension of the nanoparticles in such colloidal dispersion;
 (d) spray-drying the colloidal dispersion prepared by step (c).

3. The process according to claim 2, wherein the colloidal dispersion obtained in step (b) has a degree of neutralization (DN) of 5 to 40%.

4. The process according to claim 2, wherein the pH is adjusted with a pH increasing agent.

5. The process according to claim 4, wherein the pH increasing agent is NaOH, KOH, carbonates or hydrogencarbonates of alkali metals, ammonium carbonate, ammonium hydrogencarbonate, or $NH_3$.

6. The process according to claim 5, wherein the pH increasing agent is $NH_3$.

7. The process according to claim 3, wherein the colloidal dispersion obtained in step (b) has a degree of neutralization (DN) of 12 to 25%.

8. The process according to claim 2, wherein the colloidal dispersion obtained in step (b) has a degree of neutralization (DN) of 1 to 30%.

9. The process according to claim 1, comprising
 (a) preparing an aqueous dispersion comprising an enteric coating material;
 (b) adjusting the pH of the aqueous dispersion prepared by step (a) to a pH slightly below the solubility threshold of the enteric coating material to produce a colloidal dispersion of the enteric coating material;
 (c) preparing an aqueous suspension comprising the nanoparticles;
 (d) co-spray-drying of the colloidal dispersion prepared by step (b) together with the aqueous suspension prepared by step (c).

10. The process according to claim 1, wherein the nanoparticles used in the process have a mean size from 20 nm to 1000 nm.

11. The process according to claim 10, wherein the nanoparticles used in the process have a mean size from 100 nm to 500 nm.

12. The process according to claim 11, wherein the nanoparticles used in the process have a mean size from 200 nm to 300 nm.

13. The process according to claim 1, wherein the matrix of the nanoparticles is a biocompatible inorganic particulate material or a biocompatible organic polymer.

14. The process according to claim 13, wherein the biodegradable polymer is poly(lactic acid) (PLA), poly(glycolic acid) (PGA), polycaprolactone (PCL), a copolymer of lactic acid and glycolic acid (PLGA), a copolymer of lactic acid and caprolactone, polyepsilon caprolactone, polyhydroxy butyric acid, chitosan, a polyester, a poly(ortho) ester, a polyurethane, a polyanhydride, a polyacetal, a polydihydropyran, a polyamide, a polysaccharide or a polycyanoacrylate, blends or copolymers thereof or a derivative thereof.

15. The process according to claim 14 wherein the biodegradable polymer is PLGA.

16. The process according to claim 14, wherein said wherein the biodegradable polymer is PEG-PLGA.

17. The process according to claim 13, wherein the matrix of the nanoparticles is a biodegradable polymer.

18. The process according to claim 13, wherein the matrix of the nanoparticles is silica or surface-modified silica.

19. The process according to claim 1, wherein the enteric coating material is cellulose acetate phthalate, hydroxypropyl methylcellulose phthalate, hydroxypropyl methylcellulose acetate succinate, polyvinyl acetate phthalate, carboxymethyl ethylcellulose, cellulose acetate trimellitate, a copolymer of acrylic or methacrylic acid and an acrylic or methacrylic ester.

20. The process according to claim 19, wherein the copolymer of methacrylic acid and a methacrylate or acrylate ester is (Poly(methacrylic acid-co-methyl methacrylate) (1:1), (Poly(methacrylic acid-co-methyl methacrylate) (1:2), Poly(methacrylic acid-co-ethyl acrylate) (1:1).

21. The process according to claim 19, wherein the enteric coating material is, a copolymer of methacrylic acid and a methacrylate or a copolymer of methacrylic acid and an acrylate ester.

22. The process according to claim 1, wherein the microparticles have a mean size of 1 μm to 200 μm.

23. The process according to claim 22, wherein the microparticles have a mean size of 10 μm to 150 μm.

24. The process according to claim 23, wherein the microparticles have a mean size of 50 μm to 150 μm.

25. The process according to claim 1, wherein the product temperature during the spray drying process is below the glass transition temperature of the nanoparticles.

* * * * *